United States Patent [19]

Willson

[11] 4,215,703
[45] Aug. 5, 1980

[54] VARIABLE STIFFNESS GUIDE WIRE

[76] Inventor: James K. V. Willson, P.O. Box 2144, Mobile, Ala. 36601

[21] Appl. No.: 937,775

[22] Filed: Aug. 29, 1978

Related U.S. Application Data

[63] Continuation-in-part of Ser. No. 797,551, May 16, 1977, abandoned.

[51] Int. Cl.² ............................................. A61M 25/00
[52] U.S. Cl. .............................. 128/772; 128/DIG. 9; 128/348
[58] Field of Search .................. 128/348, 349 R, 356, 128/DIG. 9, 657, 673, 737, 772

[56] References Cited

U.S. PATENT DOCUMENTS

| | | | |
|---|---|---|---|
| 3,452,740 | 7/1969 | Muller | 128/772 |
| 3,500,820 | 3/1970 | Almen | 128/356 X |
| 3,521,620 | 7/1970 | Cook | 128/772 |
| 3,612,058 | 10/1971 | Ackerman | 128/348 |
| 3,625,200 | 12/1971 | Muller | 128/772 |
| 3,847,140 | 11/1974 | Ayella | 128/772 |

Primary Examiner—Dalton L. Truluck
Attorney, Agent, or Firm—Fisher, Christen & Sabol

[57] ABSTRACT

A guide wire capable of being adjusted to provide variable stiffness for catheterizing arterial branches comprises an elongated helical wire coil with a plurality of core wires contained within and joined to the outer wire coil at their distal ends; at their proximal ends there is a handle having two elements which are movable relative to each other connected respectively to the inner core wires and to the wire coil to vary the extent to which the coil may be flexed, by tensioning the core wires and limiting the longitudinal expansion of the coil.

16 Claims, 6 Drawing Figures

U.S. Patent  Aug. 5, 1980  Sheet 1 of 2  4,215,703
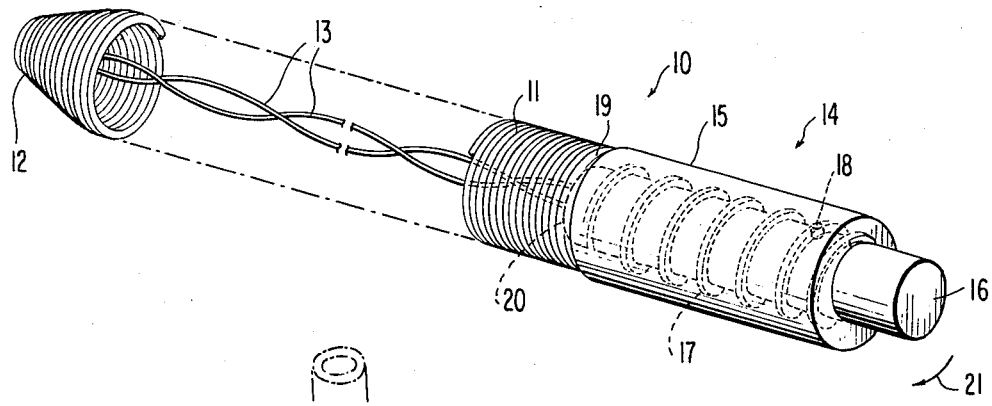
FIG.1
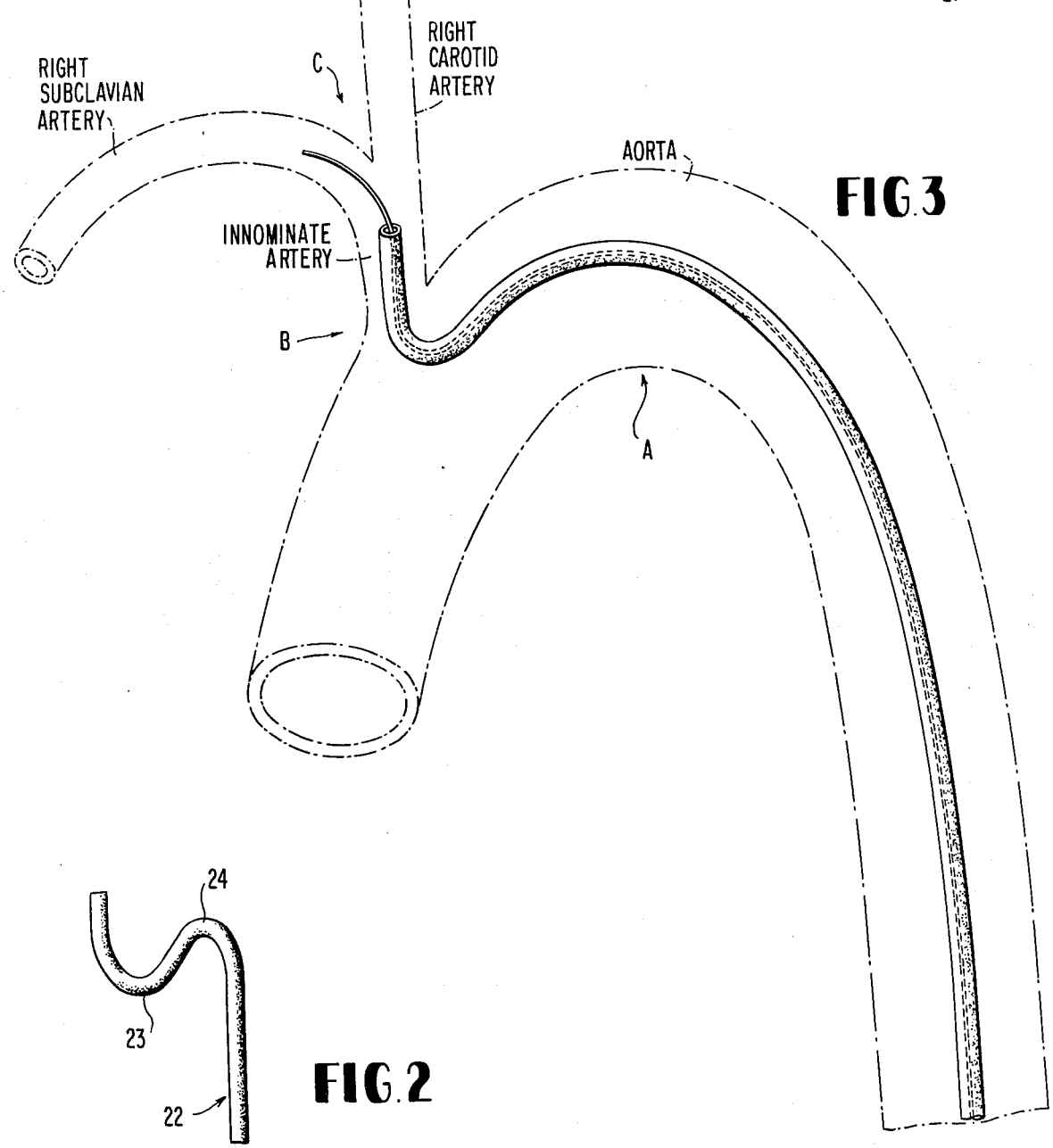
FIG.3
FIG.2

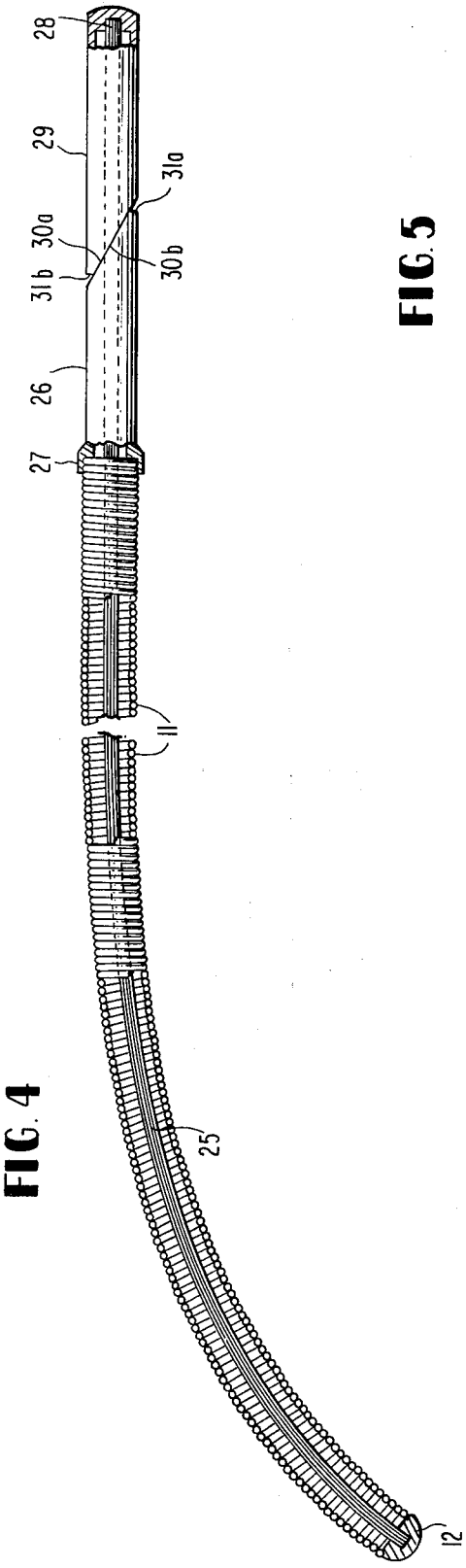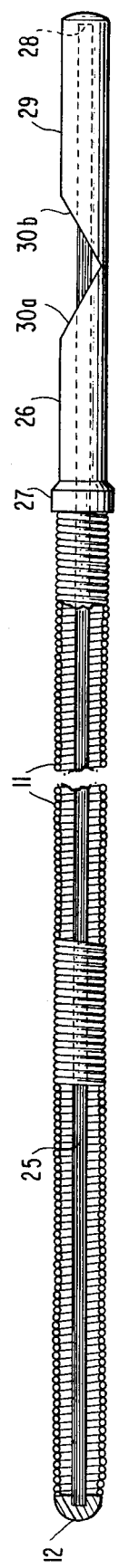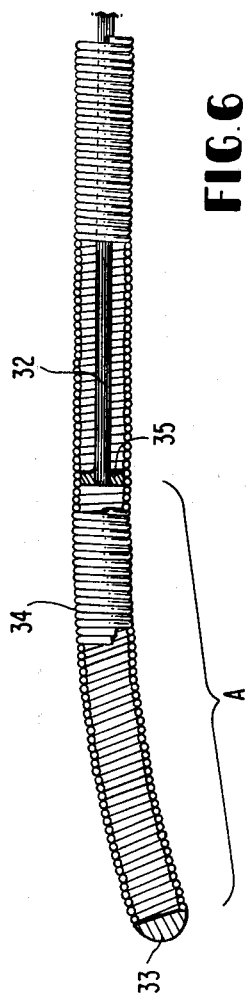
FIG. 4
FIG. 5
FIG. 6

VARIABLE STIFFNESS GUIDE WIRE

This application is a continuation-in-part of my prior copending application Ser. No. 797,551, filed May 16, 1977, now abandoned.

This invention relates to the catheterization of arterial branches by the percutaneous entry technique, and more particularly to a variable stiffness guide wire means for advancing a flexible plastic catheter into branched arteries remote from the point of entry of the catheter.

This technique involves introduction into an artery of a flexible catheter by means of a hollow needle and the advancement of the catheter into successive branched arteries by means of a guide wire which is used at the junction of each artery to probe the entrance into each successive one of the arteries. The guide wire is introduced into the branch while in a relatively limp, or supple, state and after it has been successfully inserted into the entrance it is then stiffened and the plastic catheter is advanced over the distal end of the guide wire into the branched artery.

Several types of guide wire systems are known for use in the catheterization of arteries but each of the known devices is subject to certain limitations which it is the purpose of the present invention to overcome. In one example, the guide wire comprises an outer helical core which is provided with an axial core wire which can be moved in and out in an axial direction to change the tip of the distal end of the coil from very flexible to very stiff prior to entry of the coil into the artery. However, when the wire is in a catheter which is being advanced through an arterial system the core wire can only be withdrawn in an axial direction away from the distal end; it cannot be advanced. In other words, the "floppy," or limp, distal portion of the wire created by the partial withdrawal of the core wire can be increased by a further withdrawal of the core wire, but it is impossible to decrease the extent of the "floppy" segment of the guide wire and a "floppy" segment which is in place in an artery cannot be transformed into a stiff segment. A further disadvantages with this type of guide wire is that the extent of "floppiness" or limpness cannot be varied to any intermediate degree between its extremes of limpness and stiffness.

Another form of guide wire relies for its usefulness upon being formed with its stiffness being tapered along its length whereby the distal end is extremely limp and the stiffness of the wire increases in the direction of the proximal end of the guide wire. This type of guide wire is a compromise between extreme limpness and stiffness and if the arteries are not very tortuous, this wire can be advanced far out into the artery until the stiff portion is brought into the desired segment through the curves and the catheter can be advanced over this stiff segment. The result, however, is that there are two limitations to the use of this wire: (1) it may be necessary to advance the guide wire so far that the tip is dangerously near small peripheral branches, and (2) more often, however, in older people with tortuous arteries, this wire can be advanced for only a short distance before the tip impinges on a wall with the consequent danger of perforation.

Still another form of guide wire is disclosed in a U.S. Pat. No. 3,452,742 issued to Muller. While the system disclosed in this patent is not designed for peripheral catheterization, it is of interest for the purpose of an understanding of the present invention. The Muller wire is a tip deflector wire which can be used to deflect a catheter into a branched artery when the diameter of the artery is relatively large as in the case of the aorta, but it cannot be used in the small branches, such as from the innominate into the subclavian artery. When the Muller tip is flexed to bend the catheter, considerable resistance develops between the wire and the catheter, and as the catheter is advanced forward against this resistance it is not possible to tell if the tip of the catheter is going into the lumen or into the wall of the next artery. Under these circumstances it is possible to perforate the artery or to dissect within the layers of the arterial wall. However, the Muller system is not designed to perform the functions of the variable stiffness guide wire of the present invention. Each has its own specific applications in different situations.

Therefore, it is an object of the present invention to provide a guide wire means for manipulating a flexible plastic catheter in which the flexibility of the guide wire assembly can be varied between a so called "floppy," or limp, condition similar to that of a piece of string, to a condition in which the guide wire assembly is relatively stiff, almost rigid.

To accomplish this purpose, a standard steel spring wire is wound into a helical coil having a uniform diameter which is suitable for the proposed catheter to be easily slid back and forth over the outside of the helical coil. As a non-limiting example, the diameter of the wire itself may be 0.006 in. and the diameter of the resulting coil may be 0.038 in. with the total length of the coil varying between 125–145 cm.

Extending along the entire length of the thus formed coil are anywhere between 2 and 10 (or more) core wires which, in the example given above, would have diameters each of approximately 0.004 in. At the distal end of the coil, that is, at its tip, the core wires are each secured to the interior of the exterior coil by any suitable means such as soldering, welding or any other suitable procedure. In one form, the core wires may be twisted along their length in an angular direction opposite to the direction of twist of the exterior coil; however, the pitch of the twisted core wires is considerably greater than that of the exterior coil, being in a neighborhood of about one turn per centimeter. At the proximal end, the coil wire and the respective core wires are attached to a handle mechanism which is capable of producing a twisting and axial pulling of the core wires with respect to the exterior coil.

The effect of the relative movement of the core wires with respect to the exterior coil is to put the core wires under tension which exerts a compressing force on the exterior coil which, in turn, increases the stiffness of the entire assembly, which stiffness can be varied by changing the amount of tension exerted. In a preferred form of the invention, the handle mechanism may comprise a piston and cylinder with a screw connection between the two so that rotation of the piston will cause it to be displaced in an axial direction approximately 5 mm for the turn. In this example, the core wires are attached to the piston and the coil is attached to the cylinder with the result that as the piston is rotated and moved axially relative to the cylinder a rotary and axial tension is applied to the core wires to increase, or decrease, the stiffness of the entire assembly.

Experience has also shown that equally effective results may also be obtained when the core wires are not twisted; that is to say, when they extend straight through from one end to the other of the exterior helical core. In this case, the relative rotation of the two handle elements exerts axial tension on the core wires to compress the turns of the helix tightly together to change the guide wire as a whole from its "floppy" condition to one of stiffness. Any twisting which results from the operation of the two-part handle is only incidental.

Other objects and advantages will be apparent to those skilled in the art after reading the present specification in connection with the annexed drawings, in which, FIG. 1 is an isometric view, partly cut away, of a preferred form of variable stiffness guide wire constructed in accordance with the present invention;

FIG. 2 is a view in elevation of a typical flexible plastic catheter for use with the guide wire of FIG. 1;

FIG. 3 is a schematic diagram of an arterial system illustrating manipulation of the guide wire and catheter;

FIG. 4 is a view, partly in cross-section of a modified form of guide wire, having untwisted core wires, in its "floppy" condition;

FIG. 5 is similar to FIG. 4, but shows the guide wire in its stiff condition, and;

FIG. 6 shows the distal end, partly in section, of a further modification.

In the drawings, a preferred form of variable stiffness guide wire made in accordance with the teachings of this invention is indicated generally by numeral 10 and it comprises an elongated helical closely wound wire coil 11 having an outside diameter such that it will pass freely through the lumen of the particular flexible catheter with which it is to be used. At the tip, or distal, end of this coil 12 a wire may be tapered to terminate in a rounded tip. Within this coil and extending along its entire length there are positioned a number of core wires 13 of a springy material such as piano wire which are slightly twisted along their length in a direction opposite to that of the direction of winding of the exterior coil 11 and at their distal ends they are secured to the interior of the tip of the coil 12 by soldering, welding or any other suitable means. At the proximal end of the assembly there is a handle means, indicated generally by numeral 14 which, in a preferred form of the invention, comprises a generally cylindrical outer portion 15 shaped to be conveniently manipulated by the user. Within the cylindrical element 15 there is a piston 16 which is slidable within the bore of the cylindrical element. In one form of the invention, the exterior wall of the cylindrical portion is provided with a helical groove 17 and the piston is provided with a radially outwardly extending lug 18. The proximal end of the coil 11 is secured to the cylindrical element at its forward end 19 while the proximal ends of the wire 13 are secured to the forward end 20 of piston 16. In this connection, it should be noted that the direction of rotation of the helical groove 17 is the same as the direction of rotation of the twist of the wires 13, although the pitch of the groove is significantly less than that of the pitch of the wires themselves. That is to say that, while the pitch of the wires in one example may be approximately one turn per centimeter of length, the pitch of the groove may be two turns per millimeter with the result that rotation of the piston 16 with respect to the outer handle portion 15 in one direction, as indicated by the arrow 21, will not only tend to shorten the distance between the proximal end of the wires 13 and the tip 12 of the outer coil, but will also, by twisting the wires, tend to cause the wires to further draw the tip toward the proximal end of the coil by a "bunching" of the wires themselves.

As a result, rotation of the piston in the direction of the arrow 21, not only decreases the elongation ability of the coil and thus its flexibility, but also, as a result of the aforementioned "bunching" of the core wires decreases their flexibility in bending. The combination of these two effects serves to gradually increase the stiffness of the wire assembly as a whole in proportion to the amount of rotation of the piston 16. Obviously, rotation of the piston in the opposite direction results in an increase in the flexibility of the guide wire assembly.

In operation, while the guide wire assembly just described may be used with any flexible catheter, if the initial penetration is to be made into a relatively large arterial system, it may be desirable to employ a catheter of the type identified by numeral 22 in FIG. 2, the distal end of which 23 is preformed with a slight curvature. For example, in FIG. 3, the catheterization of the right subclavin artery is diagrammatically shown in which three turns (indicated at A, B and C in FIG. 3) must be negotiated. In this particular instance, the catheter itself can be preformed with an additional curved portion 24 which will enable it to be advanced a distance sufficient to negotiate both turns A and B to the position as shown in FIG. 3 where is has been advanced through the aorta into the innominate artery. The catheter cannot be advanced through curve B by itself and therefore, the guide wire assembly 10 is advanced through the lumen of the catheter to project forwardly beyond the distal end thereof. However, once the guide wire reaches this position it must be advanced further in its limp, or "floppy," condition which is achieved, as previously described, by rotation of the piston 16 in a direction which will untwist or reduce the "bunching" of the core wires 13. In this condition the guide wire may be manipulated to enter the subclavian artery through the curve C but, once this has been achieved it is essential that the stiffness of the guide wire be increased, by appropriate rotation of the piston, to enable the catheter to be pushed forward over the guide wire. In the past, it has been attempted to perform this advancement with the use of a tapered tip having a variable stiffness; that is to say a wire having a very flexible tip with the stiffness increasing in a direction toward its proximal end. If this prior type of guide wire can be advanced far enough into the subclavian branch to bring the stiff portion of the wire through curve C then it is possible to advance the catheter forward. However, very often, particularly in older people with tortuous arteries, only the flexible tip portion can be advanced through curve C and the tip impinges on the artery wall and cannot be advanced any further. In such a situation any attempt to advance the catheter forward will not cause it to advance over the "floppy" tip portion but will only pull the entire assembly out of the branch and into the proximal portion of the aorta.

The guide wire of the present invention obviates this condition because, once the guide wire has been advanced through curve C and the handle has been manipulated to increase the stiffness of the tip portion the catheter can be advanced as far as necessary.

In the modification shown in FIGS. 4 and 5, the guide wire helix 11 may be the same as shown and described in connection with FIG. 1. However, the core may comprise a series of fine wires 25, each connected at one of their ends to the distal end of the helix 11 as by means of a lump of solder 12. These wires may vary in size and number but each, individually is a very fine gauge and extremely flexible.

Although the handle described in connection with the previous guide-wire is suitable, an alternative form of two-part handle is shown in FIGS. 4 and 5. One part 26 is connected at its forward end 27 directly to the proximal end of the wire helix 11 and is provided with a central passage through which the core wires 25 freely pass, with their ends 28 being firmly embedded in, or otherwise firmly secured to, the second part 29 of the two-part handle. In order to convert relative rotary movement of one part of the handle with respect to the other into axial displacement of the core wire ends 28 with respect to the helix 11, the inner ends of the two handle parts are provided with complementary oblique facing transverse surfaces 30a and 30b. As can be seen in FIG. 4, when these two surfaces are in coplanar relationship there is no tension on the core wires 25 and both they and the surrounding helix 11 is in a relaxed, or "floppy" state. Corresponding, as one part of the handle is turned with respect to the other, axial displacement of the ends 28 of the core wires takes place to increase tension in these wires and consequent stiffening of the guide wire as a whole, inasmuch as the distal ends of the core wires and the helix are immovably joined together at 12. It has been found in practice that with a handle having a diameter of the order of ¼ inch it is possible to set the angles of the surfaces 30a and 30b at an angle such that sufficient stiffness of the guide wire will be obtained with only a half turn of the handle part 29 with respect to part 26. A further advantage of this arrangement is that this makes it possible to secure automatic locking of the handle in the tensioned position by terminating one of the elongated ends of the oblique surfaces with the small radially extending flat surfaces 31a and 31b which, in the tensioned position of FIG. 5 will lie in abutment with one another to free the user's hands for manipulation of the guide wire by means of the handle part 26 without fear that the part 29 will slip out of position. A slight rotation of one handle part in either direction to disengage the flat surfaces immediately releases the core wires and permits the guide wire as a whole to become as "floppy" as desired by the user.

While the precise theory upon which this instrument achieves its remarkable variation in stiffness has not been scientifically investigated, it is believed that the tensioning of the core wires produces a transformation in their function. That is to say, when the core wires are relaxed (no tension being exerted on them by the two-part handle) they offer substantially no more resistance to bending as a group than would each single wire alone, considering that each wire is relatively small in diameter. Cumulatively, therefore such a bundle of fine wires offers considerably less resistance than the outer helix. However, when the core wires are put under tension the bending resistance of the assembly as a whole is increased in two ways. First, the bending resistance of the outer helix 11 is increased because along the path of curvature each turn of wire remains in contact with the adjacent turns at points lying along the inner (concave) side of the helix. At each of these contact points each turn of wire serves as a fulcrum for the adjacent turns on both sides. Thus, on the opposite (outer) side of the helix each turn of wire moves away from the adjacent turns and a line running through these points must obviously increase in length as the curvature of the helix increases. Similar, but progressively decreasing, amounts of elongation take place in parallel paths lying between the outer and inner sides of the curved helix; there being no elongation on the inner side where the abutting turns of wire act as fulcrums. As tension in the core wires is increased, compressive forces are exerted in each turn of the helix to resist the separation on the outer side of each turn.

Second, what may be even more important, since each core wire must occupy its own space in the interior of the helix the bending characteristics of the bundle of core wires as a whole progressively takes on the attributes of a rod having a diameter equivalent to that of the whole bundle of wires. It is believed that this results partly from the fact that forces in tension increase more rapidly in the core wires lying toward the outer side of the path of curvature of the helix than in those near the inner side of this path. Also, since increasing tension in the core wires lying on the outer side of the path of curvature will force all of the core wires into closer frictional contact with each other along their entire lengths it is resonable to assume that this increased frictional contact tends to increase resistance to the aforementioned differential elongation of one core wire with respect to another, and contributing to the transformation from a bundle of very flexible fine wires into something resembling a comparatively much more stiff solid rod.

In certain situations it has been found desirable to allow a small portion of the distal end of the guide wire in a permanently "floppy" condition, while still providing the major portion of the guide wire with uniform variable stiffness along its length back to the handle.

In this case, as shown in FIG. 6, the core wires 32 do not extend all the way to the closed distal end 33 of the exterior helix 34, but are joined, preferably to a single turn, of the wire helix at an intermediate location 35, leaving up to approximately 3 cm, indicated by the letter A, of the distal end in a condition which will not be affected by the core wires 32 whether relaxed or in a tensioned condition.

Obviously the arrangement of the core wires in the modification of FIG. 6 could be arranged in the twisted arrangement as shown in FIG. 1, or in the modified form of FIGS. 4 and 5. Similarly the handle arrangement of FIGS. 4 and 5 can be used with the core wires of FIG. 1 and the guide of FIG. 6 and the handle of FIG. 1 is suitable for use with the guide wires of FIGS. 4 and 5 and the guide of FIG. 6.

I claim:

1. A variable stiffness vascular guide wire for use with a flexible catheter, comprising an elongated flexible closely helically wound wire coil, an elongated stiffness control means comprising a series of core wires connected at one end to the wire coil adjacent the distal end of the guide wire and extending through substantially the entire length of the interior of the wire coil to the proximal end of the guide wire, and actuator handle means secured at said proximal end to one end of the wire coil and to the other end of the wires of the stiffness control means, said guide wire having unrestricted flexibility in bending when the wires of said stiffness control means are axially unstressed and having increasing inflexibility in bending as axial tension in said wires is increased within the confines of said wire coil, said actuator handle means including means for adjusting the relative axial displacement of the one end of the wire coil with respect to the other end of the wires of the stiffness control means to vary the tensional force in said stiffness control means.

2. The guide wire of claim 1, wherein said actuator handle means comprises two elements mounted for relative movement with respect to each other, one of the elements being connected to the proximal end of the wire coil, the other of said elements being connected to the proximal end of the stiffness control means, and means to convert said relative movement of the two elements into relative axial displacement of the respective proximal end of the wire coil and stiffness control.

3. The guide wire of claim 2, wherein said actuator handle means also includes locking means to hold the two elements in a position to exert tension on the stiffness control means.

4. The guide wire of claim 2, wherein said two elements are mounted for relative concentric rotation with respect to each other.

5. The guide wire of claim 4, wherein at least one of said two elements is provided with a cam surface obliquely related to a plane radial to the axis of rotation, the other element being provided with follower means in abutment with said cam surface.

6. The guide wire of claim 5, wherein said follower means comprises a cam surface provided on the other of the two actuator handle means elements complementary to the first mentioned cam surface.

7. The guide wire of claim 5, or 6, wherein a cam surface includes a portion lying in a plane radial to the axis of rotation to lock the two actuator handle means elements in a position to exert tension on the stiffness control element.

8. The guide wire of claim 1, wherein said stiffness control means comprises a bundle of fine metal wires loosely deployed with respect to each other along their entire lengths.

9. The guide wire of claim 2, wherein said stiffness control means comprises a plurality of metal wires extending in axially straight parallel paths and unconnected to each other along their lengths.

10. The guide wire of claim 8, or 9, wherein the diameters of wires of the stiffness control means are each less than the diameter of the wire forming the helical coil.

11. A variable stiffness vascular guide wire for use with a flexible catheter, comprising an elongated flexible helically wound wire coil, a plurality of twisted core wires extending internally through said wire coil, the distal ends of said core wires and said wire coil being joined together, and means at the proximal end of said wire coil to vary the relative positions of the proximal ends of the core wires with respect to the proximal end of said wire coil to change the tension in the core wires to vary the stiffness of the guide in either direction while in place.

12. The invention as defined in claim 11, wherein the pitch of said twisted core wires is opposite to that of said helically wound wire coil.

13. The invention as defined in claim 12, wherein said means at the proximal end of said wire coil comprises a handle comprising at least two elements movable relatively one with respect to the other, said elements being joined respectively to the wire coil and to said core wires.

14. The invention as defined in claim 13, wherein one of said two elements is mounted within the other of said two elements for axial and rotary motion.

15. The invention as defined in claim 14, wherein the cross-section of the wire forming said helically wound coil is uniform throughout its length.

16. The invention as defined in claim 15, wherein the length of the wire coil is in excess of 100 cm and the twist of said core wires is approximately 1 turn per cm.

* * * * *